(12) United States Patent
Duda et al.

(10) Patent No.: US 7,345,167 B2
(45) Date of Patent: Mar. 18, 2008

(54) METHOD FOR THE PRODUCTION OF MALEIC ANHYDRIDE

(75) Inventors: Mark Duda, Ludwigshafen (DE); Otto Machhammer, Mannheim (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 43 days.

(21) Appl. No.: 10/565,889

(22) PCT Filed: Jul. 6, 2004

(86) PCT No.: PCT/EP2004/007371

§ 371 (c)(1),
(2), (4) Date: Jan. 25, 2006

(87) PCT Pub. No.: WO2005/019148

PCT Pub. Date: Mar. 3, 2005

(65) Prior Publication Data

US 2006/0241309 A1   Oct. 26, 2006

(30) Foreign Application Priority Data

Jul. 28, 2003   (DE) .............................. 103 34 582

(51) Int. Cl.
*C07D 307/60* (2006.01)
(52) U.S. Cl. .................................. 540/259
(58) Field of Classification Search ................ 549/259
See application file for complete search history.

(56) References Cited

U.S. PATENT DOCUMENTS

| | | | |
|---|---|---|---|
| 3,474,041 A | 10/1969 | Kerr et al. | |
| 3,904,652 A | 9/1975 | Frank et al. | |
| 4,231,943 A | 11/1980 | Paradis et al. | |
| 4,342,699 A | 8/1982 | Palmer et al. | |
| 4,511,670 A | 4/1985 | Suciu et al. | |
| 4,525,471 A | 6/1985 | Bremer et al. | |
| 4,795,818 A | 1/1989 | Becker et al. | |
| 4,933,312 A | 6/1990 | Haddad et al. | |
| 5,011,945 A | 4/1991 | Taheri | |
| 5,095,125 A | 3/1992 | Haddad et al. | |
| 5,137,860 A | 8/1992 | Ebner et al. | |
| 5,158,923 A | 10/1992 | Barone | |
| 5,275,996 A | 1/1994 | Andrews et al. | |
| 5,296,436 A | 3/1994 | Bortinger | |
| 5,302,566 A | 4/1994 | Schwartz | |
| 5,498,731 A | 3/1996 | Tsurita et al. | |
| 5,532,384 A | 7/1996 | Shirley et al. | |
| 5,641,722 A | 6/1997 | Mitchell et al. | |
| 5,646,304 A | 7/1997 | Acharya et al. | |
| 5,726,327 A | 3/1998 | Acharya et al. | |
| 6,002,019 A | 12/1999 | Tamhankar et al. | |
| 6,040,460 A | 3/2000 | Bertola et al. | |
| 6,803,473 B2 | 10/2004 | Weiguny et al. | |
| 6,812,351 B2 | 11/2004 | Weiguny | |
| 2004/0014990 A1 | 1/2004 | Storck et al. | |

FOREIGN PATENT DOCUMENTS

| | | |
|---|---|---|
| DE | 391633 | 11/1990 |
| DE | 10211449 | 9/2003 |
| DE | 10211445 | 10/2003 |
| DE | 10211446 | 10/2003 |
| DE | 10211447 | 10/2003 |
| DE | 10235355 | 2/2004 |
| EP | 0029317 | 5/1981 |
| EP | 0099431 | 2/1984 |
| EP | 0690040 | 1/1996 |
| EP | 1004567 | 5/2000 |
| WO | WO-95/26817 | 10/1995 |
| WO | WO-97/12674 | 4/1997 |
| WO | WO-97/43242 | 11/1997 |
| WO | WO-01/68245 | 9/2001 |
| WO | WO-01/68626 | 9/2001 |
| WO | WO-02/22257 | 3/2002 |
| WO | WO-02/34387 | 5/2002 |

OTHER PUBLICATIONS

Ullmann's Encyclopedia of Industrial Chemistry, 6th Edition, 2000 Electronic Release, Chapter "Maleic and Fumaric Acid—Maleic Anhydride".

*Primary Examiner*—Bernard Dentz
(74) *Attorney, Agent, or Firm*—Connolly Bove Lodge and Hutz

(57) ABSTRACT

A process for preparing maleic anhydride by oxidizing n-butane in the gas phase under heterogeneous catalysis with oxygen-containing gases over a vanadium-, phosphorus- and oxygen-containing catalyst in a reactor unit at a temperature in the range from 350 to 500° C., removing the maleic anhydride formed to form a gas stream which comprises unconverted n-butane and water and recycling at least a portion of the unconverted n-butane to the reactor unit, by feeding to the reactor unit an inlet stream having an n-butane concentration of from 0.5 to 1.5% by volume and an oxygen concentration of from 5 to 21% by volume, establishing a pressure at the inlet to the reactor unit of from 0.4 to 2 MPa abs, and converting from 40 to 100% of the n-butane from the inlet stream per reactor pass.

17 Claims, No Drawings

METHOD FOR THE PRODUCTION OF MALEIC ANHYDRIDE

This application claims priority from PCT/EP04/007371 filed Jul. 6, 2004 and German application 10 334 582.5 filed Jul. 28, 2003, the disclosures of each application are incorporated herein by reference.

The present invention relates to a process for preparing maleic anhydride by oxidizing n-butane in the gas phase under heterogeneous catalysis with oxygen-containing gases over a vanadium-, phosphorus- and oxygen-containing catalyst in a reactor unit at a temperature in the range from 350 to 500° C., removing the maleic anhydride formed to form a gas stream which comprises unconverted n-butane and water and recycling at least a portion of the unconverted n-butane to the reactor unit.

Maleic anhydride is an important intermediate in the synthesis of γ-butyrolactone, tetrahydrofuran and 1,4-butanediol, which are in turn used as solvents or, for example, further processed to polymers such as polytetrahydrofuran or polyvinylpyrrolidone.

The preparation of maleic anhydride by gas phase oxidation under heterogeneous catalysis of hydrocarbons having at least four carbon atoms with oxygen over a vanadium-, phosphorus- and oxygen-containing catalyst is common knowledge and is described, for example, in Ullmann's Encyclopedia of Industrial Chemistry, $6^{th}$ edition, 1999 Electronic Release, Chapter "MALEIC AND FUMARIC ACID—Maleic Anhydride". In general, benzene or $C_4$ hydrocarbons, such as 1,3-butadiene, n-butenes or n-butane, and in particular n-butane, are used. The reaction is strongly exothermic and requires sufficient removal of the heat of reaction. In general, the reaction is carried out in a tube bundle reactor with a salt circuit or a fluidized bed. The maleic anhydride formed in the reaction is typically removed, and a gas stream remains which comprises, inter alia, the unconverted starting hydrocarbon. In what is known as the "single pass method", this gas stream is disposed of, whereas, in what is known as the "recycle pass method", the unconverted starting hydrocarbon is at least partly recycled to the reactor. Typically, this is done either by removing the starting hydrocarbon, for example by absorption, and subsequently recycling to the reactor, or directly recycling a portion of the offgas stream to the reactor. The recycle pass method thus enables a higher overall yield and therefore better utilization of the starting hydrocarbon.

The processes from the patent literature which are described hereinbelow relate to the preparation of maleic anhydride by reacting n-butane with an oxygen-containing gas over a vanadium, phosphorus- and oxygen-containing catalyst in a reaction zone in the recycle pass method, by recycling to the reaction zone at least a portion of the offgas obtained after removing the maleic anhydride formed, or removing n-butane from the offgas stream and recycling to the reaction zone.

U.S. Pat. Nos. 5,532,284, 5,646,304, 5,726,327 and 6,002,019 disclose general processes for preparing cyclic anhydrides, including maleic anhydride, by oxidizing a suitable hydrocarbon under heterogeneous catalysis with oxygen, in which the cyclic anhydride is removed from the reactor outlet stream, the remaining offgas is fed to an adsorber bed to adsorb the unconverted hydrocarbon, and the adsorbed hydrocarbon is subsequently desorbed again and recycled to the reaction zone.

A disadvantage of the processes disclosed in U.S. Pat. No. 5,532,284, 5,646,304, 5,726,327 and 6,002,019 is the obligatory use of an adsorption/desorption stage to remove and recycle the unconverted hydrocarbon. This adsorption/desorption stage is a further process step and entails corresponding capital costs and process running costs.

U.S. Pat. No. 3,904,652 discloses a process in which the n-butane concentration in the reactor inlet stream is more than 1.7% by volume, the oxygen concentration is from 3 to 13% by volume, and the oxygen-containing gas used is a gas having an oxygen content of at least 50%, preferably "pure" oxygen having a purity of at least 99.5%, and at least a portion of the offgas stream obtained after the removal of the maleic anhydride formed is recycled to the reaction zone. Since, as a consequence of the low oxygen concentration of a maximum of 13% by volume, the reactor inlet stream fed, irrespective of the n-butane concentration, is outside the explosion range, n-butane concentrations of distinctly above 1.7% by volume may also be used. The document advises against an n-butane concentration of below 1.7% by volume, since this slows the reaction rate and also requires a large amount of catalyst and a higher reaction temperature. Since the reaction pressure is described as uncritical, the reaction may be carried out at, above or below atmospheric pressure.

EP-A 0 029 317 discloses a process in which the n-butane concentration in the reactor inlet stream is from 25 to 60% by volume, the oxygen concentration is from 20 to 45% by volume, and n-butane is condensed out of the offgas stream obtained after the removal of the maleic anhydride formed, and is recycled to the reaction zone. As a consequence of the high oxygen concentration, it is necessary to feed at least one oxygen-enriched gas, which in practice ultimately means the use of "pure" oxygen. The reaction pressure specified is from 0.5 to 10 bar abs (0.05 to 1.0 MPa abs) and preferably from 1 to 3 bar abs (from 0.1 to 0.3. MPa abs).

U.S. Pat. No. 5,011,945 discloses a process in which the n-butane concentration in the reactor inlet stream is from 4 to 10 mol % (=% by volume), the oxygen concentration is from 10 to 18 mol % (=% by volume), an n-butane conversion of from 20 to 35 mol % is achieved per reactor pass and at least a portion of the offgas stream obtained after the removal of the maleic anhydride formed is recycled to the reaction zone. It is essential for the achievement of a high yield that the oxygen-containing gas used in the process mentioned is purified oxygen, in particular "pure", at least 95% oxygen. The reaction pressure is referred to as uncritical and, for practical reasons, should be in the range from 10 to 70 psia (from 0.069 to 0.48 MPa abs).

EP-A 0 099 431 discloses a process in which the n-butane concentration in the reactor inlet stream is from 2 to 10 mol % (=% by volume), the oxygen concentration is from 8 to 20 mol % (=% by volume), the oxygen-containing gas used is a gas having an oxygen content of at least 95%, preferably "pure" oxygen, a low n-butane conversion is achieved per reactor pass and at least a portion of the offgas stream obtained after the removal of the maleic anhydride formed is recycled to the reaction zone. It is essential for the achievement of a high yield that the oxygen-containing gas used in the process mentioned is purified oxygen, in particular "pure" oxygen. The reaction pressure is referred to as uncritical and, for practical reasons, should be in the range from 10 to 70 psia (from 0.069 to 0.48 MPa abs).

A disadvantage of the processes disclosed in U.S. Pat. No. 3,904,652, EP-A 0 029 317, U.S. Pat. No. 5,011,945 and EP-A 0 099 431 is the use of an oxygen-enriched gas or of "pure" oxygen. Since the oxygen-enriched gas is in practice likewise prepared by adding "pure" oxygen, it is thus necessary in all of the cases mentioned to use "pure" oxygen which is costly and inconvenient to obtain and thus expensive. In addition, in the process disclosed in EP-A 0 029 317, the relatively high concentration of n-butane of from 25 to 60% by volume and of oxygen of from 20 to 45% by volume is associated with safety disadvantages, since a reduction in the n-butane concentration into the explosive range in the event of faults has to be prevented by apparatus and control measures.

U.S. Pat. No. 4,231,943 discloses a process in which the n-butane concentration in the reactor inlet stream is from 1 to 5% by volume and more preferably from 2 to 3.5% by volume, the oxygen concentration is from 6 to 12% by volume, an n-butane conversion of only from 15 to 28% is achieved per reactor pass and a portion of the offgas stream obtained after the removal of the maleic anhydride formed is recycled to the reaction zone, and n-butane is isolated from the other portion of the offgas stream and likewise recycled to the reaction zone. The oxygen-containing gas used may be air. The reaction pressure specifed is from 10 to 1000 psig (from 0.169 to 7.0 MPa abs) and more preferably from 25 to 40 psig (from 0.27 to 0.38 MPa abs).

A disadvantage of the process disclosed in U.S. Pat. No. 4,231,943 is the low n-butane conversion per reactor pass of from 15 to 28%. This leads to a relatively high amount of n-butane in the reactor outlet stream. As a consequence of the use of air with its high content of extraneous gases, in particular nitrogen, it is necessary to avoid accumulation of these extraneous gases in the plant by discharging a correspondingly high proportion as what is known as a purge stream. This therefore means that only a certain proportion of this extraneous gas-containing offgas may be recycled directly to the reactor. In order to keep the discharge of n-butane as low as possible, n-butane is therefore isolated in the process described from the remaining proportion of the offgas and likewise recycled to the reactor. The isolation of the n-butane, which is effected, for example, by absorption and subsequent desorption, thus entails a further process step with corresponding capital costs and process running costs.

EP-A 0 690 040 discloses a process in which the n-butane concentration in the reactor inlet stream is from 1.6 to 3.0% by volume, the oxygen concentration is from 10 to 18% by volume, and at least a portion of the offgas stream obtained after the removal of the molecular anhydride formed and after scrubbing with water to remove water-soluble organic compounds is recycled to the reaction zone. The oxygen-containing gas used may be air, oxygen-enriched air or pure oxygen. The reactor inlet pressure specified is from 2.03 to 6.08 bar (from 0.203 to 0.608 MPa).

A disadvantage of the process disclosed in EP-A 0 690 040 is that it is carried out at the boundary of the explosive range or even within the explosive range. This can clearly be recognized taking into account the explosion diagram from EP-A 0 099 431 (FIG. 1). For example, the range specified in EP-A 0 690 040 of an n-butane concentration of from 1.6 to 3.0% by volume and the oxygen concentration of from 10 to 18% by volume is for the most part within the explosive range. Only by using an oxygen concentration close to the lower end of the range specified (i.e. close to 10% by volume) and/or by the use of an n-butane concentration at the lower end of the range mentioned (i.e. close to 1.6% by volume) is a safe range possible. However, as is evident from the table on page 3 of EP-A 0 690 040, it is precisely a method within the explosive range with an n-butane concentration of 2.1% by volume and an oxygen concentration of 12.2% by volume which is specified as preferred.

It is an object of the present invention to provide a process for preparing maleic anhydride by oxidizing n-butane in the gas phase under heterogeneous catalysis with oxygen, which, in relation to the progress of the reaction, is unproblematic from a safety point of view, is operated with an appropriate safety margin outside the explosion range, enables high utilization of the n-butane used by recycling of at least a portion of the unconverted n-butane, can be carried out in a simple manner and which enables a high n-butane conversion, a high selectivity and a high yield of maleic anhydride and therefore a high space-time yield.

We have found that this object is achieved by a process for preparing maleic anhydride by oxidizing n-butane in the gas phase under heterogeneous catalysis with oxygen-containing gases over a vanadium-, phosphorus- and oxygen-containing catalyst in a reactor unit at a temperature in the range from 350 to 500° C., removing the maleic anhydride formed to form a gas stream which comprises unconverted n-butane and water and recycling at least a portion of the unconverted n-butane to the reactor unit, which comprises feeding to the reactor unit an inlet stream having an n-butane concentration of from 0.5 to 1.5% by volume and an oxygen concentration of from 5 to 21% by volume, establishing a pressure at the inlet to the reactor unit of from 0.4 to 2 MPa abs, and converting from 40 to 100% of the n-butane from the inlet stream per reactor pass.

The n-butane concentration of the inlet stream fed to the reactor unit is from 0.5 to 1.5% by volume, preferably from 0.8 to 1.5% by volume, more preferably from 1 to 1.5% by volume and most preferably from 1 to 1.3% by volume.

The n-butane-containing feedstock may in principle be any n-butanic gases and liquids, for example pure n-butane or n-butane-containing mixtures of different hydrocarbons, such as 1,3-butadiene, 1-butene, 2-cis-butene, 2-trans-butene, $C_4$ mixture, 1,3-pentadiene, 1,4-pentadiene, 1-pentene, 2-cis-pentene, 2-trans-pentene, n-pentane, cyclopentadiene, dicyclopentadiene, cyclopentene, cyclopentane, $C_5$ mixture, hexenes, hexanes, cyclohexane and/or benzene.

The n-butane fraction in the entire amount of the hydrocarbon fed is preferably ≧90% and more preferably ≧95%. The n-butane used preferably stems from accompanying gas from crude oil, natural gas, steam crackers or FCC crackers.

n-Butane or n-butanic gas are generally added with control of the relative amounts, i.e. while constantly maintaining a defined ratio to the total flow rate fed at the reactor inlet and therefore the concentration. The n-butane or the n-butanic gas may be metered in in liquid or gaseous form. Preference is given to metering in in gaseous form, since this distinctly reduces the endangerment potential in the event of risk compared to metering in liquid form with subsequent evaporation of the n-butane, as a consequence of the holdup being several orders of magnitude smaller.

The oxygen concentration of the inlet stream fed to the reactor unit is from 5 to 21% by volume, preferably from 8 to 20% by volume, more preferably from 8 to 15% by volume and most preferably from 8 to 13% by volume.

The oxygen-containing feedstocks used are generally oxygen-containing gases, for example air, synthetic air, oxygen-enriched gases or else what is referred to as "pure" oxygen, i.e. stemming, for example, from air separation. Particular preference is given to using air as the oxygen-containing gas.

The proportion missing to one hundred % by volume is composed of further gases, for example nitrogen, noble gases, carbon monoxide, carbon dioxide, alkanes (e.g. propane, i-butane, pentane), alkenes (e.g. butenes), steam, oxygenated hydrocarbons (e.g. methanol, formaldehyde, formic acid, ethanol, acetaldehyde, acetic acid, propanol, propionaldehyde, propionic acid, acrolein, crotonaldehyde) and mixtures thereof. Preference is given to additionally setting a water content of from 0 to 15% by volume and preferably from 1 to 8% by volume, in the reactor inlet stream, optionally by separately feeding steam.

The pressure at the inlet to the reactor unit is from 0.4 to 2 MPa abs, preferably from 0.4 to 1.5 MPa abs, more preferably from 0.5 to 1.2 MPa abs and most preferably from 0.6 to 1 MPa abs. The inlet to the reactor unit refers to the point in the reactor unit at which the inlet stream fed comes into contact for the first time with the vanadium-, phosphorus- and oxygen-containing catalyst. The pressure specified is generally established by the pressure regulator at the reactor outlet.

The process according to the invention is carried out at a temperature of from 350 to 500° C. The temperature specified, irrespective of the type of the reactor, in each case refers to the average temperature of the heat carrier medium. Preference is given to carrying out the process according to the invention at a temperature of from 380 to 460° C. and more preferably from 380 to 440° C.

The n-butane conversion per reactor pass is from 40 to 100%, preferably from 50 to 95% and more preferably from 70 to 95%, of the n-butane from the inlet stream.

In the process according to the invention, the flow rate of the inlet stream in the reactor unit is used to set a GHSV (gas hourly space velocity) of preferably from 2000 to 10 000 $h^{-1}$ and more preferably from 3000 to 6000 $h^{-1}$, based on the volume of the inlet stream fed, normalized to 0° C. and 0.1013 MPa abs, and based on the bed volume of the catalyst sums of all reaction zones. The parameter GHSV is defined in the chapter "Definitions".

The gas phase oxidation of n-butane under heterogeneous catalysis with oxygen-containing gases in the presence of a volatile phosphorus compound over a vanadium-, phosphorus- and oxygen-containing catalyst is effected in what is referred to as a reactor unit. The term reactor unit refers to a unit composed of at least one reactor. When a plurality of individual reactors (in the sense of reactor apparatus) are connected in parallel, these are to be regarded as the equivalent of a reactor and are included hereinbelow in the term reactor.

Useful reactors in the process according to the invention are in principle all reactors which are suitable for gas phase oxidation under heterogeneous catalysis. Suitable reactors include in particular fluidized bed, Linde (spiral), plate bundle and tube bundle reactors.

In a preferred variant of the process according to the invention, the reactor unit used is a fluidized bed reactor unit. This generally comprises one or more fluidized bed reactors connected in parallel.

In another and particularly preferred variant of the process according to the invention, the reactor unit used is a tube bundle reactor unit. A tube bundle reactor consists in turn of at least one reactor tube which is surrounded by a heat carrier medium for heating and/or cooling. In general, the tube bundle reactors used in industry contain from a few hundred to several ten-thousand reactor tubes connected in parallel.

A tube bundle reactor unit may contain one or more preheating zones which heat the entering gas mixture. A preheating zone integrated in a tube bundle reactor may be realized, for example, by reactor tubes which are filled with inert material and are likewise surrounded by heat carrier medium. Suitable inert material is in principle any shaped bodies which are chemically inert, i.e. do not induce or catalyze any reaction by heterogeneous catalysis, and which have a maximum pressure drop below a particular maximum tolerable value which is specific to the plant. Suitable are, for example, oxidic materials such as aluminum oxide, silicon carbide or metallic materials such as stainless steel. Useful shaped bodies are, for example, spheres, tablets, hollow cylinders, rings, trilobes, tristars, wagonwheels, extrudates or randomly crushed shaped bodies.

In addition, when using a tube bundle reactor unit, the catalyst bed may be secured by internals, for example springs in the tube.

When the tube bundle reactor unit consists of a plurality of tube bundle reactors, for example two, three, four or more, these may be, for example, connected in parallel or connected in series. In the case of a series connection of tube bundle reactors, the starting stream of one tube bundle reactor is passed directly into the inlet of the downstream tube bundle reactor. However, it is also possible to remove and/or feed mass and/or energy between the two tube bundle reactors. For example, a portion of the gas stream or a component thereof can be withdrawn or a further gas stream can be fed or the gas stream present may be passed through a heat exchanger.

Typically, the reactor tubes in the aforementioned tube bundle reactors are manufactured from ferritic steel and typically have a wall thickness of from 1 to 3 mm. Their internal diameter is generally from 20 to 30 mm. The number of reactor tubes per tube bundle reactor is typically in the range between 5000 and 35 000, although a number above 35 000 may also be realized in particularly large plants. Within the reactor body, the reactor tubes are normally distributed homogeneously.

Suitable heat carrier media are in particular fluid heating media. It is particularly favorable to use salt melts such as potassium nitrate, potassium nitrite, sodium nitrate and/or sodium nitrite, or of low-melting metals such as sodium and also alloys of different metals. However, it is also possible to feed boiler feed water and generate steam; this may optionally be superheated or even removed at pressures above 22 MPa abs as supercritical steam.

When a tube bundle reactor unit is used in the process according to the invention, it preferably encompasses at least one and preferably at least two reaction zones cooled by a heat carrier medium. The term reaction zone refers to a region within a tube bundle reactor which contains a catalyst and in which the temperature would be kept at a uniform value in the absence of a chemical reaction as a consequence of the surrounding heat carrier medium. In general, the reaction zone is delimited by the local dimension of the heat carrier surface. For example, a tube bundle reactor having only one heat carrier circuit also encompasses only one reaction zone which, by convention, is referred to as the first reaction zone. When a tube bundle reactor unit consists, for example, of a tube bundle reactor having two separate, successive heat carrier circuits, it encompasses two reaction zones, the numbering of the reaction zones corresponding to the passage direction of the gas.

When a tube bundle reactor unit is used in the process according to the invention, it is generally advantageous to use a catalyst bed which is structured with regard to the activity in at least one of the reaction zones. This typically has a high activity in a region of low temperature and low hydrocarbon concentration and a low activity in a region in which the interaction of temperature and the hydrocarbon concentration present might result in an excessive increase in the reaction rate and in the temperature.

The structuring of the catalyst bed may be achieved by various measures, optionally in their combination. For example, it is possible to dilute the catalyst with inert material, for example with shaped bodies made of steatite, aluminum oxide, silicon carbide or another inert material. It is also possible to structure the activity by the use of catalysts having different activity. This may in turn be achieved by different shaping and/or by the use of different active compositions.

The vanadium-, phosphorus- and oxygen-containing catalysts which can be used in the process according to the invention comprise, as the catalytically active composition, an oxygen-containing vanadium-phosphorus compound or a mixture of such compounds. Suitable active compositions are described, for example, in the U.S. Pat. Nos. 5,275,996, 5,641,722, 5,137,860, 5,095,125, 4,933,312, 5,275,996 4,525,471, 5,302,566 or DE 34 29 164.

They may additionally contain what are known as promoters. Suitable promoters include the elements of groups 1 to 15 of the Periodic Table and their compounds. Suitable promoters are described, for example, in WO 97/12674 and WO 95/26817, and also in the U.S. Pat. Nos. 5,137,860, 5,296,436, 5,158,923 and 4,795,818. The promoters used are preferably elements of the compounds cobalt, molybdenum, iron, zinc, hafnium, zirconium, lithium, titanium, chromium, manganese, nickel, copper, boron, silicon, antimony, tin, niobium and bismuth, more preferably molybdenum, iron, zinc, antimony, bismuth, lithium. The promoted catalysts may contain one or more promoters. The total content of promoters in the finished catalyst is generally not more than about 5% by weight, calculated in each case as the oxide.

In the preparation of the catalysts, it is also possible to use assistants, such as tableting assistants or pore formers.

The catalysts which can be used in the process according to the invention may contain the active composition, for example, in pure, undiluted form as an "unsupported catalyst", or diluted with a preferably oxidic support material as a "mixed catalyst". Suitable support materials for mixed catalysts include, for example, aluminum oxide, silicon dioxide, aluminosilicates, zirconium dioxide, titanium dioxide or mixtures thereof. Preference is given to preparing unsupported and mixed catalysts, more preferably unsupported catalysts.

The catalyst to be used with preference in a tube bundle reactor in the process according to the invention has particles having an average diameter of at least 2 mm, preferably at least 3 mm. The average diameter of a particle refers to the average of the smallest and largest dimension between two plane-parallel plates. The catalyst to be used with preference in a fluidized bed reactor in the process according to the invention has particles having an average diameter of from 10 to 500 μm, preferably from 50 to 200 μm and more preferably from 50 to 150 μm.

Particles refer both to randomly shaped particles and also to geometrically shaped particles, known as shaped bodies. The catalyst precursors to be used in the process according to the invention preferably have shaped bodies. Suitable shaped bodies include, for example, tablets, cylinders, hollow cylinders, spheres, strands, wagonwheels or extrudates. Particular shapes, for example "trilobes" and "tristars" (see EP-A-0 593 646) or shaped bodies having at least one notch on the exterior (see U.S. Pat. No. 5,168,090) are likewise possible.

Particular preference is given to the catalyst which can be used in the process according to the invention having shaped bodies with a substantially hollow cylindrical structure. A substantially hollow cylindrical structure refers to a structure which substantially comprises a cylinder having an orifice penetrating through both end surfaces. The cylinder is characterized by two substantially parallel end surfaces and a jacket surface, and the cross section of the cylinder, i.e. parallel to the end surfaces, is of substantially circular structure. The cross section of the penetrating orifice, i.e. parallel to the end surfaces of the cylinder, is substantially likewise of circular structure. Preference is given to the penetrating orifice being disposed in the middle of the end surfaces, although this does not exclude other spatial arrangements.

The term "substantially" indicates that deviations from the ideal geometry, for example slight deformations of the circular structure, end surfaces having non-plane-parallel alignment, scratched-off corners and edges, surface roughness or notches in the jacket surface, the end surfaces or the interior surface of the penetrating drillhole in the catalyst precursor, are also included. In the context of the precision of the art of tableting, preference is given to circular end surfaces, a circular cross section of the penetrating drillhole, end surfaces having parallel alignments and macroscopically smooth surfaces.

The substantially hollow cylindrical structure may be described by an external diameter $d_1$, a height h as the separation of the two end surfaces and a diameter of the inner hole (penetrating orifice) $d_2$. The outer diameter $d_1$ of the catalyst precursor is preferably from 3 to 10 mm, more preferably from 4 to 8 mm, most preferably from 5 to 7 mm. The height h is preferably from 1 to 10 mm, more preferably from 2 to 6 mm, most preferably from 2.5 to 4.5 mm. The diameter of the penetrating orifice $d_2$ is preferably from 1 to 8 mm, more preferably from 2 to 6 mm, most preferably from 2.5 to 4 mm.

The catalyst preparation is generally a multistage process in which a catalyst precursor is initially prepared and subsequently converted by calcining to the active form. The catalyst precursors which can be used in the process according to the invention may be prepared, for example, as described in the documents U.S. Pat. Nos. 5,275,996, 5,641, 722, WO 97/12674, WO 01/68626, WO 01/68245, WO 02/22257, WO 02/34387, DE ref. no. 102 11 449.8, DE ref. no. 102 11 445.5, DE ref. no. 102 11 447.1, DE ref. no. 102 11 446.3 and DE ref. no. 102 35 355.7.

The catalysts to be used with preference in the process according to the invention have a phosphorus/vanadium atomic ratio of from 0.9 to 1.5, more preferably from 0.9 to 1.2 and most preferably from 1.0 to 1.1, an average oxidation state of vanadium of from +3.9 to +4.4 and more preferably from 4.0 to 4.3, a BET surface area of from 10 to 50 $m^2/g$ and more preferably from 20 to 40 $m^2/g$, a pore volume of from 0.1 to 0.5 ml/g and more preferably from 0.2 to 0.4 ml/g and a bulk density of from 0.5 to 1.5 kg/l and more preferably from 0.5 to 1.0 kg/l.

To ensure a long catalyst on-stream time and further increase of conversion, selectivity, yield, catalyst hourly space velocity and space-time yield, the gas phase oxidation under heterogeneous catalysis is preferably carried out in the presence of a volatile phosphorus compound. Its concentration in the feed at the reactor inlet is preferably ≧0.2 ppm by volume, i.e. $\geq 0.2 \cdot 10^{-6}$ parts by volume of the volatile phosphorus compound based on the total volume of the gas at the reactor inlet. Particular preference is given to a content of from 0.2 to 20 ppm by volume and very particular preference to from 0.5 to 10 ppm by volume. Volatile phosphorus compounds include all of those phosphorus-containing compounds which are present in gaseous form in the desired concentration under the use conditions. Suitable volatile phosphorus compounds are, for example, phosphines, phosphoric esters and the compounds described in U.S. Pat. No. 3,474,041. Particular preference is given to tri($C_1$- to $C_4$-alkyl) phosphate and very particular preference to trimethyl phosphate, triethyl phosphate and tripropyl phosphate, in particular triethyl phosphate.

The volatile phosphorus compound may be added continuously or batchwise. Preference is given to feeding continuously.

The gas stream withdrawn from the reactor unit is generally fed to a downstream process unit for removing the maleic anhydride formed. The maleic anhydride may be removed, for example, by absorption in a suitable absorbent. Suitable absorbents are, for example, water or organic solvents. In the case of absorption in water, maleic anhydride is hydrated to maleic acid. Preference is given to the absorption in an organic solvent. Suitable organic solvents are, for example, the high-boiling solvents mentioned in WO 97/43242, such as tricresyl phosphate, dibutyl maleate, high molecular weight wax, aromatic hydrocarbons having a boiling point above 140° C. or di-$C_4$-$C_8$-alkyl phthalates, such as dibutyl phthalate. In the solvents mentioned, oxygenated hydrocarbon by-products are generally also absorbed. The absorption may be carried out, for example, at a temperature of from 60 to 160° C. and a pressure of from 0.1 to 1.5 MPa abs or higher. Suitable procedures are, for instance, passing the gaseous, optionally cooled reactor effluent through a vessel filled with absorption liquid, or spraying the absorption liquid in the gas stream. Appropriate methods for extracting gas streams by washing are known to those skilled in the art.

In the process according to the invention, at least a portion of the unconverted n-butane is recycled to the reactor unit. Preference is given to recycling at least 40%, more preferably from 40 to 80% and most preferably from 50 to 75%, to the reactor unit. The recycling is indirect or direct using the gas stream which results from the removal of the maleic anhydride formed and comprises unconverted n-butane and water.

In the indirect recycling, the n-butane is removed in a virtually arbitrary manner and thus recycled to the reactor unit in enriched form. A possible process for removing the n-butane is condensation, as decribed, for example, in EP-A 0 029 317. A further and preferred process for removing the n-butane is the adsorption on a suitable absorbent with subsequent desorption, as described, for example, in U.S. Pat. Nos. 5,532,284, 5,646,304, 5,726,327 and 6,002,019.

In the direct recycling, the gas stream resulting from the removal of the maleic anhydride formed is recycled to the reactor unit in an appropriate amount. Depending on the desired reaction conditions, it is possible to decrease, leave unchanged or increase the water content of the gas stream to be recycled. In order to prevent accumulation of undesired feedstocks, by-products and inert gases, an appropriate amount of the gas stream mentioned is discharged. In general, this gas stream is fed to thermal utilization.

In the process according to the invention, preference is given to the removal of maleic anhydride from the gas stream withdrawn from the reactor unit and the recycling of at least a portion of the maleic anhydride-depleted gas stream to the reactor unit.

In a preferred embodiment of the process according to the invention, the gas phase oxidation of n-butane under heterogeneous catalysis is carried out in a tube bundle reactor. n-Butane, air, recycled n-butanic gas and tri-($C_1$- to $C_4$-alkyl) phosphate are fed continuously to the tube bundle reactor in an appropriate amount. The n-butane concentration in the reactor inlet stream is in the range from 1 to 1.5% by volume, the oxygen concentration in the range from 10 to 18% by volume. The pressure at the inlet to the tube bundle reactor is in the range from 0.4 to 1 MPa abs. In the tube bundle reactor, n-butane is converted to maleic anhydride over the vanadium-, phosphorus- and oxygen-containing catalysts at a temperature in the range from 380 to 460° C. The gas stream withdrawn from the tube bundle reactor is fed to an absorber unit in which the maleic anhydride formed is extracted by washing with a suitable absorbent. From 40 to 80% of the remaining gas stream comprising unconverted n-butane and water is recycled to the tube bundle reactor. The remaining portions of the gas stream are incinerated in an incinerator to obtain thermal energy.

The process according to the invention for preparing maleic anhydride enables, in relation to the progress of the reaction, reaction control which is unproblematic from a safety point of view with an appropriate safety margin to the explosion range. The process according to the invention also enables a high degree of utilization of the n-butane used by recycling of at least a portion of the unconverted n-butane. It can be carried out in a simple manner and enables a high n-butane conversion, a high selectivity and a high yield of maleic anhydride and therefore a high space-time yield. In the preferred form, the process according to the invention additionally enables air, which is readily available, to be used as the oxygen-containing gas. Moreover, the process according to the invention in a further preferred form enables unconverted n-butane to be recycled without using a technically complicated n-butane absorption unit.

DEFINITIONS

The parameters used in the examples, unless stated otherwise, are defined as follows:

$$\text{Space-time yield} = \frac{m_{maleic\ anhydride}}{V_{catalyst} \cdot t}$$

$$\text{Hourly space velocity} = \frac{V_{hydrocarbon}}{V_{catalyst} \cdot t}$$

$$GHSV\ (\text{gas hourly space velocity}) = \frac{V_{gas}}{V_{catalyst} \cdot t}$$

$$\text{Conversion } C_{n-butane, per\ pass} = \frac{\dot{n}_{n-butane, in} - \dot{n}_{n-butane, out}}{\dot{n}_{n-butane, in}}$$

$$\text{Selectivity } S_{maleic\ anhydride, per\ pass} = \frac{\dot{n}_{maleic\ anhydride, out}}{\dot{n}_{n-butane, in} - \dot{n}_{n-butane, out}}$$

$$\text{Yield } Y_{maleic\ anhydride, per\ pass} = C_{n-butane, per\ pass} \cdot S_{maleic\ anhydride, per\ pass}$$

$$\text{Selectivity } S_{acrylic\ acid, per\ pass} = \frac{\dot{n}_{acrylic\ acid, out}}{\dot{n}_{n-butane, in} - \dot{n}_{n-butane, out}}$$

$$\text{Selectivity } S_{acetic\ acid, per\ pass} = \frac{\dot{n}_{acetic\ acid, out}}{\dot{n}_{n-butane, in} - \dot{n}_{n-butane, out}}$$

$$\dot{n}_{n-butane, in} = \dot{n}_{n-butane, fresh} + \dot{n}_{n-butane, recycle}$$

$$\text{Yield } A_{maleic\ anhydride, overall} = A_{maleic\ anhydride, per\ pass} \cdot \frac{\dot{n}_{n-butane, in}}{\dot{n}_{n-butane, fresh}}$$

$$\text{Recycle rate} = \frac{\dot{n}_{n-butane, recycle}}{(\dot{n}_{n-butane, recycle} + \dot{n}_{n-butane, purge})}$$

$M_{maleic\ anhydride}$ Mass of maleic anhydride produced [g]

$V_{catalyst}$ Total volume which the catalyst occupies while the conversion is carried out, including the volume between the catalyst particles [l]. When a tube bundle reactor is used, $V_{catalyst}$ corresponds to the bed volume of the catalyst, summed over all reaction zones. When a fluidized bed reactor is used, $V_{catalyst}$ corresponds to the volume of the unfluidized catalyst.

t Time unit [h]

$V_{hydrocarbon}$ volume of the hydrocarbon in the gas phase at the reactor inlet normalized to 0° C. and 0.1013 MPa [I (STP)](Theoretical parameter. When a hydrocarbon is in the liquid phase under these conditions, the ideal gas law is used to calculate the hypothetical gas volume.)

$V_{Gas}$ volume of the total amount of gas at the reactor inlet normalized to 0° C. and 0.1013 MPa [I (STP)]

$C_{n\text{-}butane,\ per\ pass}$ Conversion of hydrocarbons per reactor pass $S_{maleic\ anhydride,\ per\ pass}$ Selectivity for maleic anhydride per reactor pass $Y_{maleic\ anhydride,\ per\ pass}$ Yield of maleic anhydride per reactor pass $S_{acrylic\ acid,\ per\ pass}$ Selectivity for acrylic acid per reactor pass $S_{acetic\ acid,\ per\ pass}$ Selectivity for acetic acid per reactor pass $Y_{maleic\ anhydride,\ overall}$ Overall yield of maleic anhydride in the system $\dot{n}_{n\text{-}bu\ tan\ e,in}$ n-butane mass flow rate at the reactor inlet [mol/h]

$\dot{n}_{n\text{-}bu\ tan\ e,out}$ n-butane mass flow rate at the reactor outlet [mol/h]

$\dot{n}_{n\text{-}bu\ tan\ e,fresh}$ n-butane mass flow rate which is fed to the system freshly from outside [mol/h]

$\dot{n}_{n\text{-}bu\ tan\ e,recycle}$ n-butane mass flow rate which is recycled via the cycle gas [mol/h]

$\dot{n}_{n\text{-}bu\ tan\ e,purge}$ n-butane mass flow rate which is discharged from the cycle gas as offgas [mol/h]

$\dot{n}_{maleic\ anhydride,out}$ Maleic anhydride mass flow rate at the reactor outlet [mol/h]

Recycle rate Recycle rate for n-butane $T_{SB}$ Average salt bath temperature in the reaction zone. This corresponds to the average of the temperature of the salt melt fed to the reactor and the salt melts withdrawn from the reactor.

EXAMPLES

Determination of the Average Oxidation State of the Vanadium

The average oxidation state of the vanadium was determined by potentiometric titration. For the determination, in each case from 200 to 300 mg of the sample were added under an argon atmosphere to a mixture of 15 mL of 50% sulfuric acid and 5 mL of 85% phosphoric acid, and is dissolved with heating. The solution is subsequently transferred to a titration vessel which is equipped with two Pt electrodes. The titrations are each carried out at 80° C. First, a titration is effected with a 0.1 molar potassium permanganate solution. If two stages are obtained in the potentiometric curve, the vanadium was in an average oxidation state of from +3 to less than +4. If only one stage is obtained, the vanadium was in an oxidation state of from +4 to less than +5.

In the former case (two stages/$+3 \leq V_{ox} < +4$), the solution contains no $V^{5+}$, i.e. all of the vanadium was captured titrimetrically. The consumption of the 0.1 molar potassium permanganate solution and the position of the two stages are used to calculate the amount of $V^{3+}$ and $V^{4+}$. The weighted average then gives the average oxidation state.

In the latter case (one stage/$+4 \leq V_{ox} < +5$), the consumption of the 0.1 molar potassium permanganate solution can be used to calculate the amount of $V^{4+}$. Subsequent reduction of all of the $V^{5+}$ of the resulting solution with a 0.1 molar ammonium iron(II) sulfate solution and reoxidation with 0.1 molar potassium permanganate solution allows the total amount of vanadium to be calculated. The difference between the total amount of vanadium and the amount of $V^{4+}$ gives the amount of $V^{5+}$ originally present. The weighted average then gives the average oxidation state.

Determination of the Side Crushing Strength of the Hollow Cylinders

To determine the side crushing strength, the hollow cylinders were placed in successive measurements with the rounded side surface in each case on the planar metal supporting plate of an appropriate measuring device. The two plane-parallel end surfaces were thus in the vertical direction. A planar metal die was then applied to the hollow cylinder from above at an advanced rate of 1.6 mm/min, and the variation with time of the force applied to the hollow cylinder was recorded until it broke. The side crushing strength of the individual hollow cylinder corresponds to the maximum force applied.

To determine the side crushing strength, in each case 30 individual measurements were carried out to form an average value.

Experimental Plant 1 (Single Pass)

The experimental plant 1 was equipped with a feed unit and a reactor tube. The replacement of a tube bundle reactor by a reactor tube is possible to a very great extent in the laboratory or pilot plant scale, as long as the dimensions of the reactor tube are in the region of an industrial reactor tube. The plant was operated in single pass mode.

The hydrocarbon was introduced in liquid form via a pump at a controlled mass flow rate. The oxygenous gas introduced was air at a controlled mass flow rate. Triethyl phosphate (TEP) was introduced in liquid form, dissolved in water, likewise at a controlled mass flow rate.

The tube bundle reactor unit consisted of a tube bundle reactor having one reactor tube. The length of the reactor tube was 6.5 m, the internal diameter 22.3 mm. Within the reactor tube, a multithermal element having 20 temperature measuring points was disposed in a protective tube of external diameter 6 mm. The reactor was heated by a controllable heat carrier circuit. The heat carrier medium used was a salt melt.

The reactor tube was flowed through by the reaction gas mixture from bottom to top. The upper 0.2 m of 6.5 m-long reactor tube remained unfilled. Next followed a 0.3 meter-long preheating zone which was filled with shaped steatite bodies as inert material. The preheating zone was followed by the catalyst bed which contained a total of 2180 ml of catalyst.

Directly downstream of the tube bundle reactor unit, gaseous product was withdrawn and fed to the gas chromatography on-line analysis. The mainstream of the gaseous reactor effluent was discharged from the plant.

Experimental Plant 2 (Cycle Gas)

The experimental plant 2 was experimental plant 1 supplemented by an absorber unit and cycle gas recycling. The differences to the experimental plant 1 are summarized below:

Cycle gas mode instead of "straight pass".
Catalyst charge of 2176 ml (instead of 2180 ml).
Feed of the gaseous reactor effluent to a wash column operated with water as the solvent in order to remove the soluble organic oxidation products, for example maleic anhydride, acrylic acid and acetic acid.

Discharge of a portion of the remaining gas stream as offgas and mass flow-controlled recycling of the other portion as a cycle gas stream. The cycle gas stream comprises predominantly oxygen, nitrogen, carbon monoxide, carbon dioxide and unconverted n-butane.

Preparation of the Catalyst 1

An 8 m$^3$ steel/enamel stirred tank having baffles which had been inertized with nitrogen and could be heated externally by pressurized water was initially charged with 6.1 m$^3$ of isobutanol. After the three-stage impeller stirrer had been switched on, the isobutanol was heated to 90° C. with reflux. At this temperature, the addition of 736 kg of vanadium pentoxide was commenced via the conveying screw. Once about ⅔ of the desired amount of vanadium pentoxide had been added after approx. 20 minutes, pumping-in of 900 kg of 105% phosphoric acid was commenced while continuing to add vanadium pentoxide. To clean the pump, a further 0.2 m$^3$ of isobutanol was pumped in. Subsequently, the reaction mixture was heated with reflux to from about 100 to 108° C. and left under these conditions for 14 hours. Afterwards, the hot suspension was drained into a pressure suction filter which had been inertized with nitrogen and heated beforehand, and filtered off at a temperature of about 100° C. at a pressure above the suction filter of up to 0.35 MPa abs. The filtercake was blow-dried by constantly blowing in nitrogen at 100° C. and with stirring with a height-adjustable stirrer disposed centrally within about one hour. After the filtercake had been blow-dried, it was heated to approx. 155° C. and evacuated to a pressure of 15 kPa abs (150 mbar abs). The drying was carried out down to a residual isobutanol content of <2% by weight in the dried catalyst precursor.

Subsequently, the dried powder was treated for 2 hours under air in a rotary tube having a length of 6.5 m, an internal diameter of 0.9 m and internal spiral-shaped coils. The rotation rate of the rotary tube was 0.4 rpm. The powder was conveyed into the rotary tube in an amount of 60 kg/h. The air feed rate was 100 m$^3$/h. The temperatures of the five equal-length heating zones measured directly on the exterior of the rotary tube were 250° C., 300° C., 340° C., 340° C. and 340° C. After cooling to room temperature, the VPO precursor was intimately mixed with 1% by weight of graphite and compacted in a roll compactor. The fine material in the compacted material having a particle size of <400 μm was sieved off and fed back to the compaction. The coarse material having a particle size of ≧400 μm was mixed with a further 2% by weight of graphite and tabletted in a tableting machine to 5×3×2.5 mm hollow cylinders (external diameter×height×diameter of the inner hole) having a side crushing strength of 11 N. In order to obtain the required amount of catalyst precursor, several batches were carried out.

About 2.7 t of the resulting 5×3×2.5 mm hollow cylinders were introduced in a bed height of from 9 to 10 cm continuously to a gas-permeable conveying belt of a belt calcining device consisting of two identical belt calcining apparatus connected in series and having a total of 8 calcining zones. The first 1.4 t were used to initially establish the operating parameters of the belt calcining device. Since they do not constitute a uniform material, they were not further considered in the following.

The belt calcining device was operated at atmospheric pressure. Between calcining zones 4 and 5 was disposed an encapsulated transition zone. Each of the eight calcining zones included a ventilator to generate gas circulation. Each of the eight calcining zones was supplied with the desired amount of the desired fresh gas. To obtain the desired atmospheric pressure, an appropriate amount of gas was withdrawn. The volume of the gas circulating per unit time in each calcining zone was greater than the volume of gas fed or withdrawn per unit time. Between two successive calcining zones was in each case disposed a dividing wall for reducing the gas exchange, which was open in the region of the flow of the catalyst precursor. The length of each calcining zone was 1.45 m. The rate of the conveying belt was adjusted to correspond to the desired residence time of about 2 hours per calcining zone. The individual zones were operated as illustrated in table 1:

TABLE 1

Parameters for the operation of the belt calcining device

| Zone | Temperature | Fresh gas fed |
|---|---|---|
| Calcining zone 1 | Heat to 250° C. | Air |
| Calcining zone 2 | Hold at 250° C. | Air |
| Calcining zone 3 | Hold at 250° C. | Air |
| Calcining zone 4 | Heat to 310° C. | Air |
| Transition zone | Cool to 200° C. | Air |
| Calcining zone 5 | Heat to 425° C. | $N_2$ |
| Calcining zone 6 | Hold at 425° C. | $N_2/H_2O$ vapor (1:1) |
| Calcining zone 7 | Hold at 425° C. | $N_2/H_2O$ vapor (1:1) |
| Calcining zone 8 | Cool to room temperature | $N_2$ |

In this way, approx. 1.3 t of finished catalyst 1 were prepared continuously. A representative average sample of this catalyst had the following data:

| | |
|---|---|
| average oxidation state of the vanadium ($V_{ox}$): | 4.15 |
| side crushing strength (SDF): | 9.4 N |

Preparation of Catalyst 2

The dried catalyst precursor powder was prepared as described for catalyst 1.

Subsequently, the dried powder was treated for 2 hours under air in a rotary tube having a length of 6.5 m, an internal diameter of 0.9 m and internal spiral-shaped coils. The rotation rate of the rotary tube was 0.4 rpm. The powder was conveyed into the rotary tube in an amount of 60 kg/h. The air feed rate was 100 m$^3$/h. The temperatures of the five equal-length heating zones measured directly on the exterior of the rotary tube were 250° C., 300° C., 340° C., 340° C. and 340° C. After cooling to room temperatu the VPO precursor was intimately mixed with 1% by weight of graphite and compacted in a roll compactor. The fine material in the compacted material having a particle size of <400 μm was sieved off and fed back to the compaction. The coarse material having a particle size of ≧400 μm was mixed with a further 2% by weight of graphite and tabletted in a tableting machine to 5.5×3×3 mm hollow cylinders (external diameter×height×diameter of the inner hole) having a side crushing strength of 10 N. In order to obtain the required amount of catalyst precursor, several batches were carried out.

The 5.5×3×3 mm hollow cylinders were placed continuously in a bed height of from 9 to 10 cm on a gas-permeable conveyor belt of a belt calcining apparatus composed of two identical belt calcining apparatus connected in series and having a total of eight calcining zones. The calcining was effected as described for catalyst 1.

A representative sample was taken. This had the following data:

| | |
|---|---|
| average oxidation state of the vanadium (Vox): | 4.14 |
| side crushing strength (SCS): | 8 N |

Preliminary Remark on Examples 1 to 11

Examples 1 to 11 were carried out in the experimental plant 1 described using the catalyst 1 described. The analytical results reported were obtained after a catalyst running time of about 300 hours. Under the predefined parameters, the average salt bath temperature $T_{SB}$ was in each case adjusted to attain a conversion $C_{n\text{-}butane,\ per\ pass}$ of about 80%, so that the individual examples are comparable to each other.

Even when the experimental plant 1 was operated in single pass mode, the composition of the reactor inlet stream and the process parameters in the reactor with regard to the n-butane concentration, the oxygen concentration and the pressure were similar to a corresponding method with n-butane recycling (recycle pass mode). The examples are therefore representative and transferable in relation to the operation of the reactor and the performance data, in particular conversion, selectivity, yield and space-time yield, even for a corresponding method with n-butane recycling (recycle pass method).

Examples 1 to 5 (Comparative Examples)

In these examples, the oxygen concentration was varied from initially 19.9% by volume to 12.4% by volume at a constant reactor inlet pressure of 0.33 MPa abs and constant n-butane concentration in the reactor inlet stream of 2.0% by volume. The variation was effected by partially substituting air by nitrogen.

The results reproduced in table 2 show that when the oxygen concentration was reduced from 19.9% by volume to 12.4% by volume, and therefore when the partial oxygen pressure was reduced correspondingly, the maleic anhydride selectivity falls by 3.9% and the maleic anhydride yield by 2.4%. The space-time yield is reduced by 4.2 g/l h. At the same time, the average salt bath temperature required for the desired n-butane conversion of about 80% rises by 15° C. from 404 to 419° C., which leads to distinctly more rapid deactivation of the catalyst and therefore a significantly shorter running time.

Examples 6 to 8 (Comparative Examples)

In these examples, the oxygen concentration was varied from initially 19.9% by volume to 15.0% by volume at a constant partial oxygen pressure of 0.066 MPa and constant n-butane concentration in the reactor inlet stream of 2.0% by volume. This was associated with an increase in the reactor inlet pressure of from 0.33 to 0.44 MPa abs. The variation was effected by partially substituting air by nitrogen.

The results reproduced in table 3 show that when the oxygen concentration is reduced from 19.9% by volume to 15.0% by volume at a constant partial oxygen pressure, and therefore the reactor inlet pressure is increased correspondingly, the maleic anhydride selectivity falls by 1.3% and the maleic anhydride yield by 0.9%, when the n-butane concentration in the reactor inlet stream is 2.0% by volume. The space-time yield was reduced by 1.6 g/lh.

Example 9 (Comparative Example) and Examples 10 and 11

In these examples, the oxygen concentration was varied from initially 19.9% by volume to 12.6% by volume at a constant partial oxygen pressure of 0.066 MPa and the n-butane concentration in the reactor inlet stream from initially 2.0% by volume to 1.2% by volume. This was associated with an increase in the reactor inlet pressure of from 0.33 to 0.52 MPa abs. The variation was effected by partially substituting air by nitrogen, and also by reducing the amount of n-butane fed.

The results reproduced in table 4 show that the oxygen concentration can be reduced from 19.9% by volume to 12.6% by volume at a constant partial oxygen pressure and therefore at a corresponding increase in the reactor inlet pressure without a significant loss in maleic anhydride yield and without an increase in the formation of the secondary components acrylic acid and acetic acid when the n-butane concentration in the reactor inlet stream is at the same time reduced from 2.0% by volume to 1.2% by volume. The small decrease in the maleic anhydride yield of 0.2%, which is calculated from the experimental data, is more than compensated by the enormous advantage that, in contrast to an oxygen concentration of 19.9% by volume at which it is necessary to add pure oxygen in a technically complicated and expensive manner, it is possible to add air as the oxygen-containing gas at an oxygen concentration of 15.2% by volume and below. Despite a possibly slightly lower maleic anhydride yield, the process according to the invention in its entirety thus has a distinct advantage over the prior art processes as a consequence of the use of air which is now possible.

Preliminary Remark on Examples 12 to 25

Examples 12 to 25 were carried out in the experimental plant 2 described using the catalyst 2 described. The analytical results reported were obtained after a catalyst running time of about 300 hours. Under the predefined parameters, the average salt bath temperature TSB was in each case adjusted to attain a conversion $C_{n\text{-}butane,\ per\ pass}$ of about 85%, so that the individual examples are comparable to each other.

In these examples, the amount of recycled offgas was varied at constant n-butane concentration and constant GHSV. For comparison, examples 12, 13, 19 and 20 were carried out without recycling.

The results reproduced in table 5 show that recycling of the n-butane results in achievement of an increase in the maleic anhydride yield $Y_{maleic\ anhydride,\ overall}$ of from 58% to 63.1%. In addition, the salt bath temperature can be reduced from 416° C. down to 394° C. The amount of triethyl phosphate can be reduced in the process according to the invention and results in a further improvement in the economic viability of the process. The space-time yield decreases only slightly at constant n-butane loading.

The results reproduced in table 6 show that recycling of the n-butane in the process according to the invention additionally result in an increase in the space-time yield up to 130.5 g/lh, since safe operation of the reactor is still possible even at higher n-butane loadings. It is possible, by changing the operating parameters of the single pass process to the parameters of the cycle gas mode, to start up to a stable operating point achieving a comparable space-time yield, but the maleic anhydride yield $Y_{maleic\ anhydride,\ overall}$ in the process according to the invention is 5.4 abs % and 9.6 rel % higher than in the single pass process.

TABLE 2

Variation of the oxygen concentration at a constant reactor inlet pressure of 0.33 MPa abs and constant n-butane concentration in the reactor inlet stream of 2.0% by volume

|  | Example 1 | Example 2 | Example 3 | Example 4 | Example 5 |
|---|---|---|---|---|---|
| Reactor inlet pressure [MPa abs] | 0.33 | 0.33 | 0.33 | 0.33 | 0.33 |
| Oxygen concentration [% by vol.] | 19.9 | 16.4 | 15.3 | 13.7 | 12.4 |
| n-Butane concentration [% by vol.] | 2.0 | 2.0 | 2.0 | 2.0 | 2.0 |
| $C_{n\text{-butane, per pass}}$ [%] | 79.4 | 80.3 | 80.3 | 80.4 | 80.4 |
| $T_{SB}$ [° C.] | 404 | 412 | 412 | 416 | 419 |
| $Y_{maleic\ anhydride,\ per\ pass}$ [%] | 56.5 | 55.4 | 54.9 | 54.6 | 54.1 |
| $S_{maleic\ anhydride,\ per\ pass}$ [%] | 71.2 | 69.0 | 68.4 | 68.0 | 67.3 |
| $S_{acrylic\ acid,\ per\ pass}$ + $S_{acetic\ acid,\ per\ pass}$ [%] | 3.3 | 2.9 | 2.9 | 2.8 | 2.6 |
| Space-time yield [g/lh] | 98.9 | 97.0 | 96.1 | 95.6 | 94.7 |

During the entire experimental series, the following parameters were kept constant:

| | |
|---|---|
| GHSV = | 2000 l (STP)/$l_{catalyst}$ · h |
| Concentration of triethyl phosphate (TEP) = | 2 ppm by volume |
| Concentration of steam = | 3% by volume |

TABLE 3

Variation of the oxygen concentration at a partial oxygen pressure of 0.066 MPa abs and constant n-butane concentration in the reactor inlet stream of 2.0% by volume

|  | Example 6 | Example 7 | Example 8 |
|---|---|---|---|
| Reactor inlet pressure [MPa abs] | 0.33 | 0.42 | 0.44 |
| Oxygen concentration [% by vol.] | 19.9 | 15.4 | 15.0 |
| n-Butane concentration [% by vol.] | 2.0 | 2.0 | 2.0 |
| $C_{n\text{-butane, per pass}}$ [%] | 79.8 | 80.2 | 80.0 |
| $T_{SB}$ [° C.] | 407 | 404 | 404 |
| $Y_{maleic\ anhydride,\ per\ pass}$ [%] | 55.6 | 55.0 | 54.7 |
| $S_{maleic\ anhydride,\ per\ pass}$ [%] | 69.7 | 68.5 | 68.4 |
| $S_{acrylic\ acid,\ per\ pass}$ + $S_{acetic\ acid,\ per\ pass}$ [%] | 3.1 | 3.4 | 3.5 |
| Space-time yield [g/lh] | 97.3 | 96.3 | 95.7 |

During the entire experimental series, the following parameters were kept constant:

| | |
|---|---|
| GHSV = | 2000 l (STP)/$l_{catalyst}$ · h |
| Concentration of triethyl phosphate (TEP) = | 2 ppm by volume |
| Concentration of steam = | 3% by volume |

TABLE 4

Variation in the oxygen concentration at a constant partial oxygen pressure of 0.066 MPa and variation of the n-butane concentration in the reactor inlet stream

|  | Example 9 | Example 10 | Example 11 |
|---|---|---|---|
| Reactor inlet pressure [MPa abs] | 0.33 | 0.44 | 0.52 |
| Oxygen concentration [% by vol.] | 19.9 | 15.2 | 12.6 |
| n-Butane concentration [% by vol.] | 2.0 | 1.5 | 1.2 |
| GHSV [l (STP)/$l_{catalyst}$ · h] | 2000 | 2600 | 3300 |
| $C_{n\text{-butane, per pass}}$ [%] | 80.2 | 80.0 | 80.3 |
| $T_{SB}$ [° C.] | 407 | 408 | 412 |
| $Y_{maleic\ anhydride,\ per\ pass}$ [%] | 55.7 | 55.6 | 55.5 |
| $S_{maleic\ anhydride,\ per\ pass}$ [%] | 69.4 | 69.5 | 69.1 |
| $S_{acrylic\ acid,\ per\ pass}$ + $S_{acetic\ acid,\ per\ pass}$ [%] | 3.1 | 3.2 | 3.1 |
| Space-time yield [g/lh] | 97.5 | 97.3 | 97.1 |

During the entire experimental series, the following parameters were kept constant:

| | |
|---|---|
| Concentration of triethyl phosphate (TEP) = | 2 ppm by volume |
| Concentration of steam = | 3% by volume |

TABLE 5

Variation of the recycle rate at constant n-butane loading of 44 l (STP)/lh

|  | Example 12 | Example 13 | Example 14 | Example 15 | Example 16 | Example 17 | Example 18 |
|---|---|---|---|---|---|---|---|
| Recycle rate [%] | 0 | 0 | 38.6 | 54.5 | 65.1 | 74.1 | 79.4 |
| Reactor inlet pressure [MPa abs] | 0.33 | 0.85 | 0.85 | 0.85 | 0.85 | 0.85 | 0.85 |
| Oxygen concentration [% by vol.] | 19.9 | 19.9 | 17.8 | 16.3 | 14.3 | 11.5 | 8.4 |
| n-butane concentration [% by vol.] | 2.0 | 1.0 | 1.0 | 1.0 | 1.0 | 1.0 | 1.0 |
| GHSV [l (STP)/$l_{catalyst}$ · h] | 2200 | 4400 | 4400 | 4400 | 4400 | 4400 | 4400 |

TABLE 5-continued

Variation of the recycle rate at constant n-butane loading of 44 l (STP)/lh

| | Example 12 | Example 13 | Example 14 | Example 15 | Example 16 | Example 17 | Example 18 |
|---|---|---|---|---|---|---|---|
| $C_{n\text{-butane, per pass}}$ [%] | 84.5 | 84.6 | 84.8 | 84.5 | 84.8 | 84.8 | 85.1 |
| TSB [° C.] | 416 | 394 | 394 | 396 | 399 | 410 | 420 |
| $Y_{maleic\ anhydride,\ overall}$ [%] | 58.0 | 57.9 | 61.5 | 62.6 | 62.3 | 63.1 | 61.6 |
| Space-time yield [g/lh] | 111.7 | 111.5 | 111.5 | 110.3 | 108.3 | 107.8 | 104.6 |
| TEP [ppm by vol.] | 2.5 | 1.5 | 1.5 | 1.5 | 1.5 | 1.5 | 1.5 |

During the entire experimental series, the following parameters were kept constant:

| | |
|---|---|
| Concentration of steam = | 3% by volume |

TABLE 6

Variation of the recycle rate at constant n-butane loading of 53 l (STPL)/lh

| | Example 19 | Example 20 | Example 21 | Example 22 | Example 23 | Example 24 | Example 25 |
|---|---|---|---|---|---|---|---|
| Recycle rate [%] | 0 | 0 | 39 | 50 | 60 | 64.5 | 79.4 |
| Reactor inlet pressure [MPa abs] | 0.33 | 0.85 | 0.85 | 0.85 | 0.85 | 0.85 | 0.85 |
| Oxygen concentration [% by vol.] | 19.9 | 19.9 | 17.1 | 15.8 | 14.1 | 13.2 | 8.7 |
| n-butane concentration [% by vol.] | 2.4 | 1.2 | 1.2 | 1.2 | 1.2 | 1.2 | 1.2 |
| GHSV [l (STP)/$l_{catalyst}$ · h] | 2200 | 4400 | 4400 | 4400 | 4400 | 4400 | 4400 |
| $C_{n\text{-butane, per pass}}$ [%] | runaway | 84.6 | 85 | 84.6 | 85.1 | 85.2 | 84.8 |
| TSB [° C.] | n.d. | 392 | 397 | 399 | 402 | 405 | 419 |
| $Y_{maleic\ anhydride,\ overall}$ [%] | n.d. | 56.1 | 60.0 | 60.7 | 61.5 | 60.8 | 59.2 |
| Space-time yield [g/lh] | n.d. | 129.6 | 130.5 | 129.6 | 129.4 | 127.1 | 121.3 |
| TEP [ppm by vol.] | 2.5 | 1.5 | 1.5 | 1.5 | 1.5 | 1.5 | 1.5 | n.d.: not determined

During the entire experimental series, the following parameters were kept constant:

| | |
|---|---|
| Concentration of steam = | 3% by volume |

We claim:

1. A process for preparing maleic anhydride by oxidizing n-butane in the gas phase under heterogeneous catalysis with oxygen-containing gases over a vanadium-, phosphorus- and oxygen-containing catalyst in a reactor unit at a temperature in the range from 350 to 500° C., removing the maleic anhydride formed to form a gas stream which comprises unconverted n-butane and water and recycling at least a portion of the unconverted n-butane to the reactor unit, which comprises feeding to the reactor unit an inlet stream having an n-butane concentration of from 0.5 to 1.5% by volume and an oxygen concentration of from 5 to 21% by volume, establishing a pressure at the inlet to the reactor unit of from 0.6 to 1 MPa abs, and converting from 40 to 100% of the n-butane from the inlet stream per reactor pass.

2. A process as claimed in claim 1, wherein an inlet stream having an n-butane concentration of from 1 to 1.5% by volume is fed to the reactor unit.

3. A process as claimed in claim 1, wherein an inlet stream having an oxygen concentration of from 10 to 18% by volume is fed to the reactor unit.

4. A process as claimed in claim 1, wherein a GHSV of from 2000 to 10,000 h$^{-1}$, based on the volume of the inlet stream fed, normalized to 0° C. and 0.1013 MPa abs, and based on the bed volume of the catalyst summed over all reaction zones, is established in the reactor unit via the flow rate of the inlet stream.

5. A process as claimed in claim 1, wherein the oxygen-containing gas used is air.

6. A process as claimed in claim 1, wherein the heterogeneously catalyzed gas phase oxidation is carried out in the presence of a volatile phosphorus compound.

7. A process as claimed in claim 1, wherein the reactor unit used is a fluidized bed reactor unit.

8. A process as claimed in claim 1, wherein the reactor unit used is a tube bundle reactor unit having at least one reaction zone cooled by a heat carrier medium.

9. A process as claimed in claim 8, wherein a tube bundle reactor unit is used which has at least two reaction zones cooled by a heat carrier medium.

10. A process as claimed in claim 1, wherein at least 40% of the unconverted n-butane is recycled to the reactor unit.

11. A process as claimed in claim 10, wherein from 40 to 80% of the unconverted n-butane is recycled to the reactor unit.

12. A process as claimed in claim 1, wherein maleic anhydride is removed from the gas stream withdrawn from the reactor unit and at least a portion of the gas stream depleted in maleic anhydride is recyled to the reactor unit.

13. A process as claimed in claim 2, wherein an inlet stream having an oxygen concentration of from 10 to 18% by volume is fed to the reactor unit.

14. A process as claimed in claim 2, wherein a GHSV of from 2000 to 10,000 $h^{-1}$, based on the volume of the inlet stream fed, normalized to 0° C. and 0.1013 MPa abs, and based on the bed volume of the catalyst summed over all reaction zones, is established in the reactor unit via the flow rate of the inlet stream.

15. A process as claimed in claim 3, wherein a GHSV of from 2000 to 10,000 $h^{-1}$, based on the volume of the inlet stream fed, normalized to 0° C. and 0.1013 MPa abs, and based on the bed volume of the catalyst summed over all reaction zones, is established in the reactor unit via the flow rate of the inlet stream.

16. A process as claimed in claim 6, wherein a GHSV of from 2000 to 10,000 $h^{-1}$, based on the volume of the inlet stream fed, normalized to 0° C. and 0.1013 MPa abs, and based on the bed volume of the catalyst summed over all reaction zones, is established in the reactor unit via the flow rate of the inlet stream.

17. A process as claimed in claim 2, wherein the oxygen-containing gas used is air.

* * * * *